(12) United States Patent
Morgan et al.

(10) Patent No.: US 6,258,583 B1
(45) Date of Patent: *Jul. 10, 2001

(54) **TYPE II RESTRICTION ENDONUCLEASE, HPY188I, OBTAINABLE FROM *HELICOBACTER PYLORI* J188 AND A PROCESS FOR PRODUCING THE SAME**

(75) Inventors: Richard D. Morgan, Middleton, MA (US); Qing Xu, Nashville, TN (US)

(73) Assignees: New England Biolabs, Inc., Beverly, MA (US); Vanderbilt University, Nashville, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/393,245

(22) Filed: Sep. 10, 1999

(51) Int. Cl.$^7$ ............................... C12N 9/22; C12N 15/55
(52) U.S. Cl. ...................... 435/199; 435/320.1; 536/23.2
(58) Field of Search ................................ 435/199, 320.1; 536/23.2

(56) References Cited

U.S. PATENT DOCUMENTS 5,200,333   4/1993   Wilson ............................... 435/172.3

OTHER PUBLICATIONS

Roberts, J. R., et al. (1999) Nucl. Acids Res. 27(1), 312–313.*
Xu, Q., et al. (1997) J. Bacterol. 179(21), 6807–6815.*
Xu, Q. (2000) Rebase Ref Num 6039.*
Endow, et al., J. Mol. Biol. 112:521 (1977).
Waalwijk, et al., Nucleic Acids Res., 5:3231 (1978).
Gingeras, et al., Proc. Natl. Acad. Sci., 80:402 (1983).
Gingeras, et al., Nucleic Acids Res. 5:4105 (1978).
Sanger, et al., Proc. Natl. Acad. Sci., 74:5463 (1977).
Brown, et al., J. Mol. 140:143 (1980).
Lunnen, et al., Gene, 74:25 (1988).
Staden, Nucleic Acids Res. 10:4731 (1982).
Devernx, et al., Nucleic Acids Res. 12:387 (1984).
Atlschul, et al., J. Mol. Biol. 215:403 (1990).
Gish, et al., Nature Genet., 3:266 (1993).
Brooks, et al., Nucleic Acids Res. 17:979 (1989).
Schildkraut, Genetic Engineering, vol. 6, 117–139, J.K. Setlow and A. Hollaender, eds. (1984).

* cited by examiner

Primary Examiner—Charles L. Patterson, Jr.
(74) Attorney, Agent, or Firm—Gregory D. Williams; James Gregory Cullem

(57) ABSTRACT

In accordance with the present invention, there is provided a novel restriction endonuclease and its DNA obtainable from *Helicobacter pylori* J188 (NEB#1174), hereinafter referred to as "Hpy188I", which endonuclease:

(1) recognizes the nucleotide sequence 5'-TCNGA-3' in a double-stranded DNA molecule as shown below, $$5'\text{-TCN}\downarrow\text{GA-3'}$$
$$3'\text{-AG}\uparrow\text{NCT-5'}$$

(wherein G represents guanine, C represents cytosine, A represents adenine, T represents thymine and N represents either G, C, A, or T);

(2) cleaves said sequence in the phosphodiester bonds between the N and G as indicated with the arrows; and (3) cleaves double-stranded PhiX174 DNA to produce 18 fragments, including fragments of 1331, 813, 572, 525, 396, 302, 293, 219 base pairs, and 10 fragments smaller than 200 base pairs.

10 Claims, 4 Drawing Sheets

FIG. 3B

```
   1 TGA TAT AAT GGA TTT AGG AAA CGC CAA TAA AAT TAA AAA GGT TCA AAA ATA GTG TTA TCT CTC CCT TTG ATA
   1                                                                       (M)  L   S   L   P   L   I
  73 GAA AAA CGC CCT TTT TTA AAT CAC GAA CGC ATC AAA TTA CAT AGT TTT TCG CAA GTT AAA GCG TAT TTT GAC
   8  E   K   R   P   F   L   N   H   E   R   I   K   L   H   S   F   S   Q   V   K   A   Y   F   D
 145 ACA CTC AAT TTT GAC ACA AGT CAT TTT GTT AAT TCT AAT GAT ATT TGC ACC CCA TTA GAT TGT GTG AAA GAA
  32  T   L   N   F   D   T   S   H   F   V   N   S   N   D   I   C   T   P   L   D   C   V   K   E
 217 ATG ATA GAC ACT ATC CCA AGC GAT TTT TTT AAA CAA GAA CAT TTA AAA ATT TTA GAT TGT TGT TGT GGG AAT
  56  M   I   D   T   I   P   S   D   F   F   K   Q   E   H   L   K   I   L   D   C   C   C   G   N
 289 GGG AAT TTT TTT GCT TAT TTA GAG ACT AAG ACT TCT CTA AAC AAT CTG TAT TTT AAT GAG ATT AAC CCT AAA
  80  G   N   F   F   A   Y   L   E   T   K   T   S   L   N   N   L   Y   F   N   E   I   N   P   K
 361 CGC ATT GAG CAT GTT AAA AAA TAT TTT GGG AGC AAT ATC CAT TTA AGC TGT AAG GAT TTT TTA AAA TTT GAT
 104  R   I   E   H   V   K   K   Y   F   G   S   N   I   H   L   S   C   K   D   F   L   K   F   K
 433 AGG GCT ACG CTT TAT GAC TTA ATC GTG GCT AAC CCA CCT TTT GCT AAA TTT AAT GCG CTA GGT CGC ACT TCT
 128  R   A   T   L   Y   D   L   I   V   A   N   P   P   F   A   K   F   N   A   L   G   R   T   S
 505 AAA AAT CAT AAT CTG GCA AGA GAC TTT ATT AAA AAA GCC TTA GAG CTT ACA AAA AAT GGG GGT TAT ATT CTA
 152  K   N   H   N   L   A   R   D   F   I   K   K   A   L   E   L   T   K   N   G   G   Y   I   L
 577 TTC ATT GTG CCT AAT CAT TGG ATG AGT TTT TCA GAT AGG AAT GTT TTA CCC AAC TTA CTC TCA CAA TAT CAA
 176  F   I   V   P   N   H   W   M   S   F   S   D   R   N   V   L   P   N   L   L   S   Q
 649 TTT ATC CAT CTT AAT ATT GGC GGA GCT AAA AAA TAC TTT AAA AAA GTT GGC TCA TCT TTC ACT TGG TTT TTA
 200  F   I   H   L   N   I   G   G   A   K   K   Y   F   K   K   V   G   S   S   F   T   W   F   L
 721 TTG CAA AAA GTC CCT AAT CAA AAA AGT TTT AGC GTA GAA AAT CAT TAT GTT TTA AAA GAC AGA CAA AGA GTT
 224  L   Q   K   V   P   N   Q   K   S   F   S   V   E   N   H   Y   V   L   K   D   R   Q   R   V
 793 TCG CTT AGA ACT CAT TTA AAT TTC ATT CCC TTG TAT TTA AAC GAA TTG GTT TGT AGC ATT TTA GAT AAA ACG
 248  S   L   R   T   H   L   N   F   I   P   L   Y   L   N   E   L   V   C   S   I   L   D   K   T
 865 ATC AAT AAT ACT CAT TTA CCT ACC TAT AAA ATA GAA ACG ACA AGC TTT CTA CAC AGG ACA ACC AAG AAA GAA
 272  I   M   N   T   H   L   P   T   Y   K   I   E   T   T   S   F   L   H   R   T   T   K   K   E
 937 TTT TTA TCG CCC ATT CAA AAT AAG GAC TAC CCT TAT AAG ATT ATC CAT ACC CCT AGT CAA GTC GTA TAT AGT
 296  F   L   S   P   I   Q   N   K   D   Y   P   Y   K   I   I   H   T   P   S   Q   V   V   Y   S
1009 AAA ATC CCC CAC AAA TAC CAA GAA GGC TAT AAA GTC TTT TTA TCT TTG ACT AAT CAA TAC AGC ACA TTT ATT
 320  K   I   P   H   K   Y   Q   E   G   Y   K   V   F   L   S   L   T   N   Q   Y   S   T   F   I
1081 GAT AAT TGC GGC ATG ACA CCA AGC AAT GCG TTT GTG CGT TGC AAA AAC TAC GAA GAG GCC TTA AAA ATT AAA
 344  C   N   C   G   M   T   Q   S   I   A   F   V   R   C   K   N   Y   E   E   A   L   K   I   K
1153 ACC GAA TTA GAT AAT GAG ATT TAT TTA TTT CTT AAT AAT CTC ACT CGT TAT GGA AAT TTT AAT AAC ATT AGA
 368  T   E   L   D   N   E   I   Y   L   F   L   N   N   L   T   R   Y   G   N   F   N   N   I   R
1225 GTG TTA CAG CAT TTA CCT TTA TTA GAA AGT ATT GTT CTA AAC AAG CAA GAA TTA GAA TTT ATC CAA AAA TTT
 392  V   L   Q   H   L   P   L   L   E   S   I   V   L   N   K   Q   E   L   E   F   I   Q   K   F
1297 AAT GAG GCG TAT TAT GGC AAA AAG AAA GAG CGA TAT AAT TTT AAA GAG TGT TGA TGA TTT AAA AGA TGA AAT
 416  N   E   A   Y   Y   G   K   K   K   E   R   Y   N   F   K   E   C   *
   1                      M   A   K   R   K   S   D   I   I   L   K   S   V   D   D   L   K   D   E   I
1369 TGA TTA CAA GGA CTT TGA ATA CAA AGA GTA TTT TAA TTT ATT ATG CGA ATT AGT CCC TAA TAA TAG TTT GGA
  21  D   Y   K   D   F   E   Y   K   E   Y   F   N   L   L   C   E   L   V   P   N   N   S   L   E
1441 AAA ATT AGA AAT CAA CGC CAT TGA TGA AAA GAA TAT GAA AAA CGA AGG ACT TGT ATA TGT GTT TGT TAT TCA
  45  K   L   E   I   N   A   I   D   E   K   N   M   K   N   E   G   L   V   Y   V   F   V   I   Q
1513 AGG TAA AAT TTT TAA AAT CGG TCA TAG TAT TAC GCC CAT CAC AAA GCG AGT GCA ATC TTA TAA TTG CGG CAA
  69  G   K   I   F   K   I   G   H   S   I   T   P   I   T   K   R   V   Q   S   Y   N   C   G   K
1585 AGT AGA ATA TCG TAA AAA TGG CAC TTG CTC CAC AAC AAA TTA TTT TGT ATT GCA ATC GCT CTT AAA GAT AAA
  93  V   E   Y   R   K   N   G   T   C   S   T   T   N   Y   F   V   L   Q   S   L   L   K   I   N
1657 TAA AAT CGT ACA AGT GTA TGC ATT TTT TCC AGA ACA ACC TAC CTA TAC CCT ATT TGG TAA AAC TTA CCA AGA
 117  E   I   V   Q   V   Y   A   F   F   P   E   Q   P   T   Y   T   L   F   G   K   T   Y   Q   D
1729 TAG TTT TTC AAC TTC TAA AAG GGC TGA GAA TGT GAT TTT AGA AAA TTT TAT TAA AAA TCA TAA TAA AAA ACC
 141  S   F   S   T   S   K   R   A   E   N   V   I   L   E   N   F   I   K   N   H   N   K   K   P
1801 TAT CGG ATG CAC ACA GAC TTA A
 165  I   G   C   T   Q   T   *
```

TYPE II RESTRICTION ENDONUCLEASE, HPY188I, OBTAINABLE FROM HELICOBACTER PYLORI J188 AND A PROCESS FOR PRODUCING THE SAME

BACKGROUND OF THE INVENTION

The present invention relates to a new Type II restriction endonuclease, Hpy188I, obtainable from *Helicobacter pylori* J188, and to the process for producing the same.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. The majority of restriction endonucleases recognize sequences of 4 to 6 nucleotides in length, although recently a small number of restriction endonucleases which recognize 7 or 8 uniquely specified nucleotides have been isolated. Most recognition sequences contain a dyad axis of symmetry and in most cases all the nucleotides are uniquely specified. However, some restriction endonucleases have degenerate or relaxed specificities in that they recognize multiple bases at one or more positions in their recognition sequence, and some restriction endonucleases recognize asymmetric sequences. HaeIII, which recognizes the sequence 5'-GGCC-3', is an example of a restriction endonuclease having a symmetrical, non-degenerate recognition sequence, while HaeII, which recognizes 5'-(Pu)GCGC(Py)-3' typifies restriction endonucleases having a degenerate or relaxed recognition sequence. Endonucleases with symmetrical recognition sequences generally cleave symmetrically within or adjacent to the recognition site, while those that recognize assymmetric sequences tend to cleave at a distance of from 1 to 18 nucleotides away from the recognition site. More than two hundred unique restriction endonucleases have been identified among several thousands of bacterial species that have been examined to date.

Endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences 5'-(AT)GGCC(AT)-3', 5'-(Pu)GCGC(Py)-3' and 5'-GGCC-3' respectively. *Escherichia coli* RY13, on the other hand, synthesizes only one enzyme, EcoRI, which recognizes the sequence 5'-GAATTC-3'.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecule and cleaving them in each place that the recognition sequence occurs. The disintegration that results inactivates many of the infecting genes and renders the DNA susceptible to further degradation by exonucleases.

A second component of restriction systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always modified, by virtue of the activity of its modification methylase and it is therefore insensitive to the presence of the endogenous restriction endonuclease. It is only unmodified, and therefore identifiably foreign, DNA that is sensitive to restriction endonuclease recognition and attack. More than 3000 restriction endonucleases have been isolated from various bacterial strains. Of these, more than 200 recognize unique sequences, while the rest share common recognition specificities. Restriction endonucleases which recognize the same nucleotide sequence are termed "isoschizomers." Although the recognition sequences of isoschizomers are the same, they may vary with respect to site of cleavage (e.g., XmaI v. SmaI, Endow, et al., *J. Mol. Biol.* 112:521 (1977); Waalwijk, et al., *Nucleic Acids Res.* 5:3231 (1978)) and in cleavage rate at various sites (XhoI v. PaeR7I, Gingeras, et al., *Proc. Natl. Acad. Sci. U.S.A.* 80:402 (1983)).

There is a continuing need for novel type II restriction endonucleases. Although type II restriction endonucleases which recognize a number of specific nucleotide sequences are currently available, new restriction endonucleases which recognize novel sequences provide greater opportunities and ability for genetic manipulation. Each new unique endonuclease enables scientists to precisely cleave DNA at new positions within the DNA molecule, with all the opportunities this offers.

SUMMARY OF THE INVENTION

In accordance with the present invention, there is provided a novel restriction endonuclease obtainable from *Helicobacter pylori* J188 (NEB#1174), hereinafter referred to as "Hpy188I", which endonuclease:

(1) recognizes the nucleotide sequence 5'-TCNGA-3' in a double-stranded DNA molecule as shown below,

(wherein G represents guanine, C represents cytosine, A represents adenine, T represents thymine and N represents either G, C, A, or T);

(2) cleaves said sequence in the phosphodiester bonds between the N and G as indicated with the arrows; and (3) cleaves double-stranded PhiX174 DNA to produce 18 fragments, including fragments of 1331, 813, 572, 525, 396, 302, 293, 219 base pairs, and 10 fragments smaller than 200 base pairs.

The present invention further relates to a process for the production of the novel restriction endonuclease Hpy188I. This process comprises either culturing *Helicobacter pylori* J188 under conditions suitable for expressing Hpy188I, collecting the cultured cells, obtaining a cell-free extract therefrom and separating and collecting the restriction endonuclease Hpy188I from the cell-free extract, or culturing a transformed host, such as *E. coli*, containing the genes for the Hpy188I methylase and endonuclease, collecting the cultured cells, obtaining a cell-free extract therefrom and separating and collecting the restriction endonuclease Hpy188I from the cell-free extract.

DETAILED DESCRIPTION OF THE INVENTION

Figure 1:
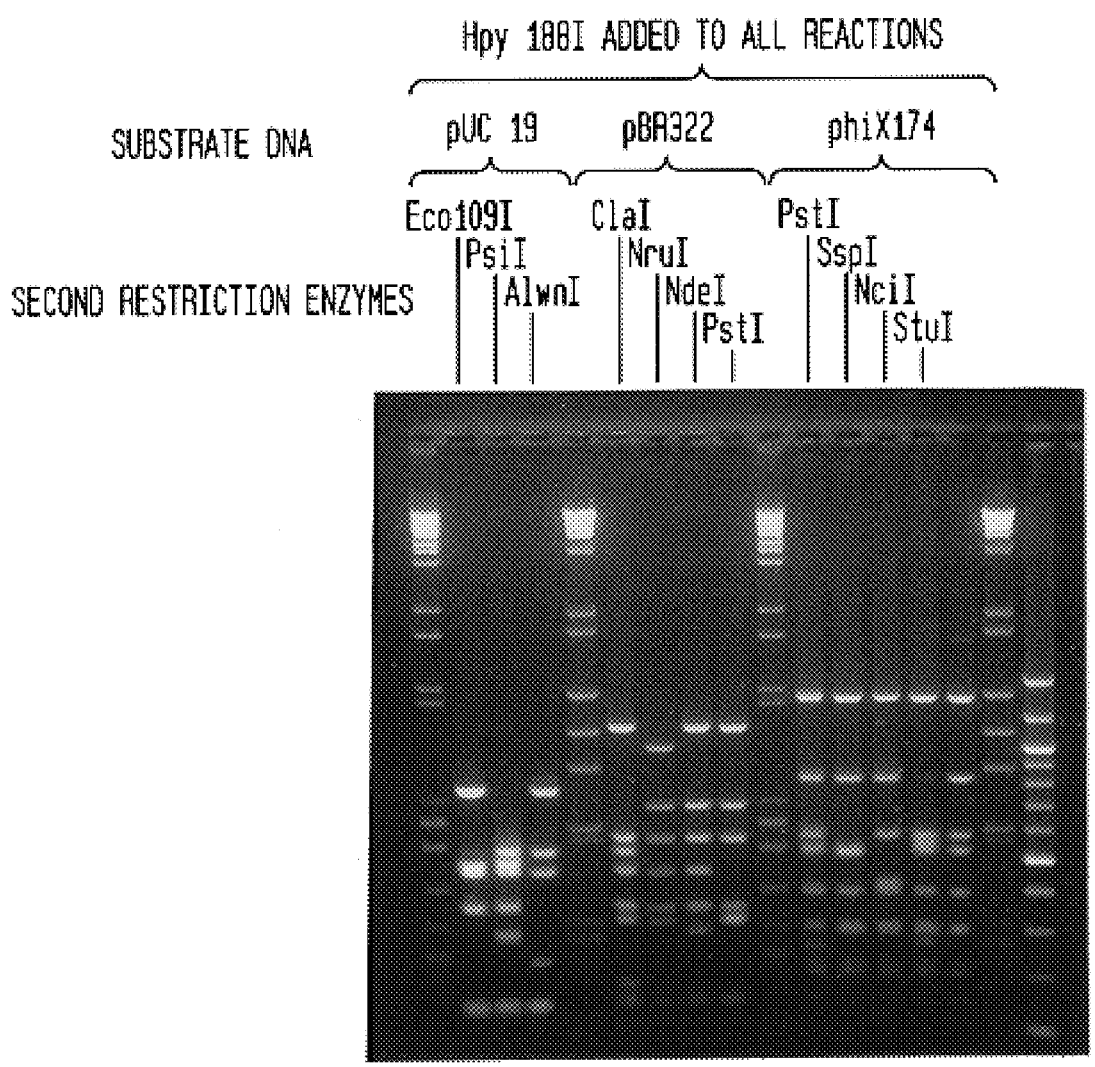
FIG. 1—Agarose gel showing Hpy188I cleavage of various DNAs.

The recognition sequence of the endonuclease of the present invention may be determined by mapping the locations of several Hpy188I cleavage sites in various DNAs and comparing the DNA sequences of these regions for homology, then comparing the predicted cleavage fragments of the putative recognition sequence with the observed restriction fragments produced by Hpy188I cleavage of various DNAs. The endonuclease Hpy188I was found to cleave PhiX174 DNA more than ten times, producing fragments of approximately 1350, 800, 575, 525, 400, 300 and 225 bp along with a number of smaller fragments. The location of several cut sites were mapped to approximate positions of 1075 and 2400 (the 1350 bp fragment) and 4225 and 5025 (the 800 bp fragment) by simultaneously digesting PhiX174 DNA with Hpy188I and with endonucleases which cleave at known positions, such as SspI, BsrBI, NciI, SacII, StuI and PstI (FIG. 1). The approximate size of several of the larger DNA fragments produced by Hpy188I digestion of PhiX174 DNA were entered into the program SITES (Gingeras, et al., *Nucl. Acids Res.* 5:4105 (1978)), which generates potential recognition sequences for the input data by comparing the fragment sizes which would result from cleavage of the DNA at any given recognition pattern with the input fragment sizes. One such potential pattern generated was TCNGA, which occurs in PhiX174 DNA at positions consistant with the mapping data obtained, i.e. at positions 1071 and 2402, and 4223 and 5036, as well as 14 other sites. The size of fragments predicted from cleavage at TCNGA sites in PhiX174, pBR322, pUC19, T7 and lambda DNAs matched the observed size of fragments from cleavage of these DNAs with Hpy188I, from which we conclude that Hpy188I recognizes the sequence 5'-TCNGA-3'.

The point of cleavage within the Hpy188I recognition sequence may be determined through dideoxy sequencing analysis of the terminal base sequence obtained from Hpy188I cleavage of a suitable DNA substrate (Sanger, et al., *PNAS* 74:5463–5467 (1977) Brown, et al., *J. Mol. Biol.* 140:143–148 (1980)). By the above referenced method (FIG. 2, exemplified in Example II) is was found that Hpy188I cleaves the phosphodiester bond between the unspecified nucleotide N and the G in the recognition sequence 5'-TCN/GA-3' to produce a 1 base 3' extension, as indicated by the arrows:

The enzyme of the present invention also has the following properties:

(a) Optimal buffer composition: Of the four standard NEBuffers tested, the optimal endonuclease reaction buffer was NEBuffer IV. Relative activity in NEBuffer I was approximately 90%, NEBuffer II was 50%, while relative activity in NEBuffer III was approximately 10%.

In accordance with the present invention, Hpy188I is obtained by culturing *Helicobacter pylori* J188 and recovering the endonuclease from the cells. A sample of *Helicobacter pylori* J188 has been deposited under the terms and conditions of the Budapest Treaty with the American Type Culture Collection (ATCC) on Jan. 3, 2001, and received ATCC Patent Accession No. PTA-2878.

In accordance with the present invention, isoschizomers of Hpy188 have been identified, which are substantially similar to Hpy188I (having greater than about 90% homology at the amino acid level), in other Helicobacter strains, such as *Helicobacter pylori* J166. Of nine different Helicobacter strains studied, two of which the DNA sequence is known, it was observed that the genes for various given restriction endonucleases and methylases are present and functional in a number, though not all, of these strains. The presence of Hpy188I or isoschizomers thereof, can be readily assertained in various Helicobacter strains by any of several methods. The genomic DNA of the strain may be prepared (as outlined in the example below) and digested with the enzyme of the current application. If Hpy188I cleaves the genomic DNA, that strain does not contain an active Hpy188I methyl-transferase, whereas if the DNA is not cleaved, it is likely the Hpy188I methyl-transferase is present in that strain, and thus potentially the Hpy188I endonuclease as well. The Hpy188I genes may also be obtained form various Helicobacter strains by PCR amplification, using the sequence of the Hpy188I endonuclease and methylase genes (SEQ ID NO:1 AND SEQ ID NO:3) provided in this application as the guide to PCR primer design. Helicobacter strains containing the enzymes of the present invention may also be identified by the methods exemplified in Schildkraut, *Genetic Engineering*, Volume 6, 117–139, J. K. Setlow and A. Hollaender, eds. (1984), which methods comprise growing cells, obtaining a cell-free extract of proteins from the cells and assaying that extract for the presence of Hpy188I endonuclease activity.

For recovering the enzyme of the present invention *Helicobacter pylori* J188 may be grown using any suitable technique. For example, *Helicobacter pylori* J188 may be grown in Brucella broth media (BBL Microbiology Systems, Cockeysville, Md.) incubated at 37° C. Cells in the late logarithmic stage of growth are collected by centrifugation and either disrupted immediately or stored frozen at −70° C.

The Hpy188I enzyme can be isolated from *Helicobacter pylori* J188 cells by conventional protein purification techniques. For example, cell paste is suspended in a buffer solution and treated by sonication, high pressure dispersion or enzymatic digestion to allow extraction of the endonuclease by the buffer solution. Intact cells and cellular debris are then removed by centrifugation to produce a cell-free extract containing Hpy188I. The Hpy188I endonuclease is then purified from the cell-free extract by ion-exchange chromatography, affinity chromatography, molecular sieve chromotography, or a combination of these methods to produce the endonuclease of the present invention.

The endonuclease of the present invention along with its corresponding methylase may also be obtained using recombinant DNA techniques, such as the methylation selection technique disclosed by Wilson, et al., U.S. Pat. No. 5,200, 333. As an example, DNA from a bacterial strain which contains an R-M system, such as *Helicobacter pylori*, is purified, partially digested with suitable type II endonucleases, and ligated to an appropriate cleaved, dephosphorylated cloning vector. The ligated DNA is transformed into an appropriate host, such as *E. coli*, the transformants are pooled and the population of cloning vectors are purified to form libraries. The library of clones is then challenged by digesting with an endonuclease which will selectively destroy vectors which do not contain and express the methylase of the R-M system being cloned. Vectors which contain and express the methylase gene of interest will be modified at the endonuclease recognition sites of the challenging endonuclease and thus be immune from cleavage. The challenged clone pools are then transformed back into the appropriate host to recover the undigested, presumably methylase expressing clones. The transformants may be screened for endonuclease activity or cycled through further rounds of purification and selection. Finally, individual transformants are selected and their DNA purified. These clones are analyzed for resistance to cleavage by the endonuclease of interest and for common insert DNA. Cell extracts prepared from transformants which demonstrate endonuclease resistance are assayed in vitro for methyltransferase and endonuclease activities.

The present invention is further illustrated by the following Examples. These Examples are provided to aid in the understanding of the invention and are not construed as a limitation thereof.

The references cited above and below are herein incorporated by reference.

EXAMPLE I

Production of Hpy188I Endonuclease

*Helicobacter pylori* J188 strain NEB#1174 was grown in Brucella broth media. The cells were incubated anaerobically under 5% $CO_2$ at 37° C. until late logarithmic stage. The cells were then harvested by centrifugation and stored frozen at −70° C.

10 grams of the cells obtained above were suspended in 40 mls buffer A (20 mM Tris-HCl, 0.1 mM EDTA, 1 mM dithiothreitol, 5% glycerol, pH 7.6 at 25° C.) adjusted to 50 mM NaCl. The cell suspension was sonicated until approximately 50 mg protein per gram of cells was released. The lysate was centrifuged at 15,000 rpm for 20 minutes at 4° C. in a Beckman JA17 rotor. 42 ml of supernatant was obtained containing approximately 50,000 units of Hpy188I and 500 mg of soluble protein.

The supernatant solution was applied to a 20 ml Heparin Hyper-D column (Biosepra, Marlborough, Mass.) equilibrated in buffer A adjusted to 50 mM NaCl. A 40 ml wash of buffer A adjusted to 50 mM NaCl was applied, then a 200 ml linear gradient of NaCl from 50 mM to 1M in buffer A was applied and fractions of 4 ml were collected. Fractions were assayed for Hpy188I endonuclease activity by incubation with 1 μg Lambda DNA (NEB) in 50 μl NEBuffer 4 for one hour at 37° C. Hpy188I activity eluted at 0.3M to 0.38M NaCl.

The Heparin Hyper-D column fractions containing the Hpy188I activity were pooled, diluted to 50 mM NaCl in buffer A and applied to a 1 ml Mono-S column (Pharmacia, Piscataway, N.J.) equilibrated in buffer A adjusted to 50 mM NaCl. The column was washed with 2 mls buffer A adjusted to 50 mM NaCl. The protein solution was eluted with a 50 ml gradient of 50 mM to 1M NaCl in buffer A and fractions were tested for Hpy188I activity. The Hpy188I activity eluted between 0.26M and 0.3M NaCl. The Hpy188I activity was pooled, diluted to 50 mM NaCl, and applied to a PolyCatA column (Custom LC Inc., Houston, Tex.) equilibrated in buffer A adjusted to 50 mM NaCl. The column was washed with buffer A adjusted to 50 mM NaCl and the Hpy188I enzyme was eluted with a 50 ml gradient of 50 mm to 0.6 M NaCl in buffer A. The Hpy188I activity eluted between 0.3 M and 0.38 M NaCl. The PolyCatA pool of Hpy188I was diluted to 0.1 M NaCl, passed through a 1 ml Mono-Q column (Pharmacia) onto a 3 ml Heparin-TSK column (Toso-Haas, Philadelphia, Pa.). The Mono-Q column was then removed from the FPLC apparatus and a 50 ml linear gradient from 0.1 M to 0.6 M NaCl in buffer A was applied to the Heparin-TSK column. The Hpy188I activity eluted between 0.38 M to 0.42 M NaCl and contained approximately 14,000 units of endonuclease activity. The Hpy188I obtained was substantially pure and free of contaminating endonuclease and exonuclease activities. A portion of this endonuclease was used to obtain N-terminal amino acid sequence information. To the remainder was added bovine serum albumin as a stabilizer to a final concentration of 200 μg/ml and the Hpy188I enzyme was dialyzed against storage buffer (50% glycerol, 50 mM NaCl, 20 mM Tris-HCl, 0.1 mM dithiothreitol, pH 7.5).

Activity Determination

Hpy188I activity: Samples of from 1 to 10 μls were added to 50 μls of substrate solution consisting of 1×NEBuffer 4 containing 1 μg Lambda phage DNA. The reaction was incubated at 37° C. for 5 to 60 mins. The reaction was terminated by adding 5 μls of a stop solution (50% glycerol, 50 mM EDTA pH 8.0, and 0.02% Bromophenol Blue). The reaction mixture was applied to a 1% agarose gel and electrophoresed. The bands obtained were identified in comparison with DNA size standards.

Unit Definition: One unit of Hpy188I is defined as the amount of Hpy188I required to completely cleave 1.0 μg of Lambda DNA in a total reaction volume of 50 μl NEBuffer 4, supplemented with 100 μg/ml bovine serum albumin, within one hour at 37° C.

Optimal Buffer Conditions: For optimum Hpy188I activity NEBuffer 4 (50 mM potassium acetate, 20 mM Tris-acetate, 10 mM magnesium acetate, 1 mM dithiothreitol (pH 7.9 at 25° C.), supplemented with 100 ug/ml bovine serum albumin, was used.

EXAMPLE II

Determination of the Hpy188I Cleavage Site

The location of Hpy188I cleavage relative to the recognition sequence was determined by cleavage of a primer extension product, which was then electrophoresed alongside a set of standard dideoxy sequencing reactions produced from the same primer and template. M13mp18 DNA was employed as the template utilizing an Hpy188I recognition site at position 1353, conveniently located 54 bp 3' of a priming site for a primer designated M13 Q1-Q2 (5'-dGGTCGCTGAGGCTTGCAGGG-3' (SEQ ID NO:5)) and 53 bp 3' of a priming site on the opposite strand for a primer designated M13 Q2-2 (5'-dCGTTTAATGGAAACTTCCTC-3' (SEQ ID NO:7)).

Sequencing Reactions

The sequencing reactions were performed using the Sequenase version 2.0 DNA sequencing kit (Amersham Life Science) with modifications for the cleavage site determination. The template and primer (for the M13 Q1-Q2 primer) were assembled in a 0.5 mL eppendorf tube by combining 10 μl dH20, 4 μl 5×sequencing buffer (200 mM Tris pH 7.5, 250 mM NaCl, 100 mM MgCl2), 4 μl M13mp18 single stranded DNA (2 μg) and 2 μl of primer (M13 Q1-Q2 at 3.2 μM concentration). The template and primer (for the M13 Q2-2 primer) were assembled in a 0.5 mL eppendorf tube by combining 10 µl dH20, 4 µl 5×sequencing buffer (200 mM Tris pH 7.5, 250 mM NaCl, 100 mM MgCl2), 4 µl M13mp18 double stranded DNA (2 µg) and 2 µl of primer (M13 Q2-2 at 3.2 µM concentration). The primer-template solutions were incubated at 65° C. for 2 minutes, then cooled to 37° C. over 20 minutes in a beaker of 65° C. water on the benchtop to anneal the primer. The labeling mix and sequenase were diluted according to manufacturer's instructions. The annealed primer and template tube was placed on ice. To this tube were added 2 µl 100 mM DTT, 4 µl diluted dGTP labeling mix, 1 µl [$\alpha$-$^{33}$P] dATP (2000 Ci/mmole, 10 mCi/ml) and 4 µl diluted T7 Sequenase polymerase. The reaction was mixed and incubated at room temperature for 5 minutes. 3.5 µl of this reaction was then transferred into each of four tubes containing 2.5 µl termination mix for the A, C, G and T sequencing termination reactions. To the remaining reaction was added to 17 µl of Sequence Extending Mix, which is a mixture of dNTPs (no ddNTPs) to allow extension of the primer through and well beyond the Hpy188I site with no terminations to create a labeled strand of DNA extending through the Hpy188I recognition site for subsequent cleavage. The reactions were incubated 5 minutes at 37° C. To the A, C, G and T reactions were added 4 µl of stop solution and the samples were stored on ice. The extension reaction was then incubated at 70° C. for 20 minutes to inactivate the DNA polymerase (Sequenase), then cooled on ice. 10 µl of the extension reaction was then placed in a 0.5 ml eppendorf tube. To this tube was added 1 µl (approximately 1 unit) Hpy188I endonuclease. This enzyme digest reaction was mixed and then incubated at 37° C. for 30 minutes, following which 6 µl of stop solution was added and mixed. The sequencing reaction products were electrophoresed on an 6% Bis-Acrylamide sequencing gel, with the Hpy188I digestions of the extension reaction next to the set of sequencing reactions produced from the same primer and template combination.

Results

Figure 2:
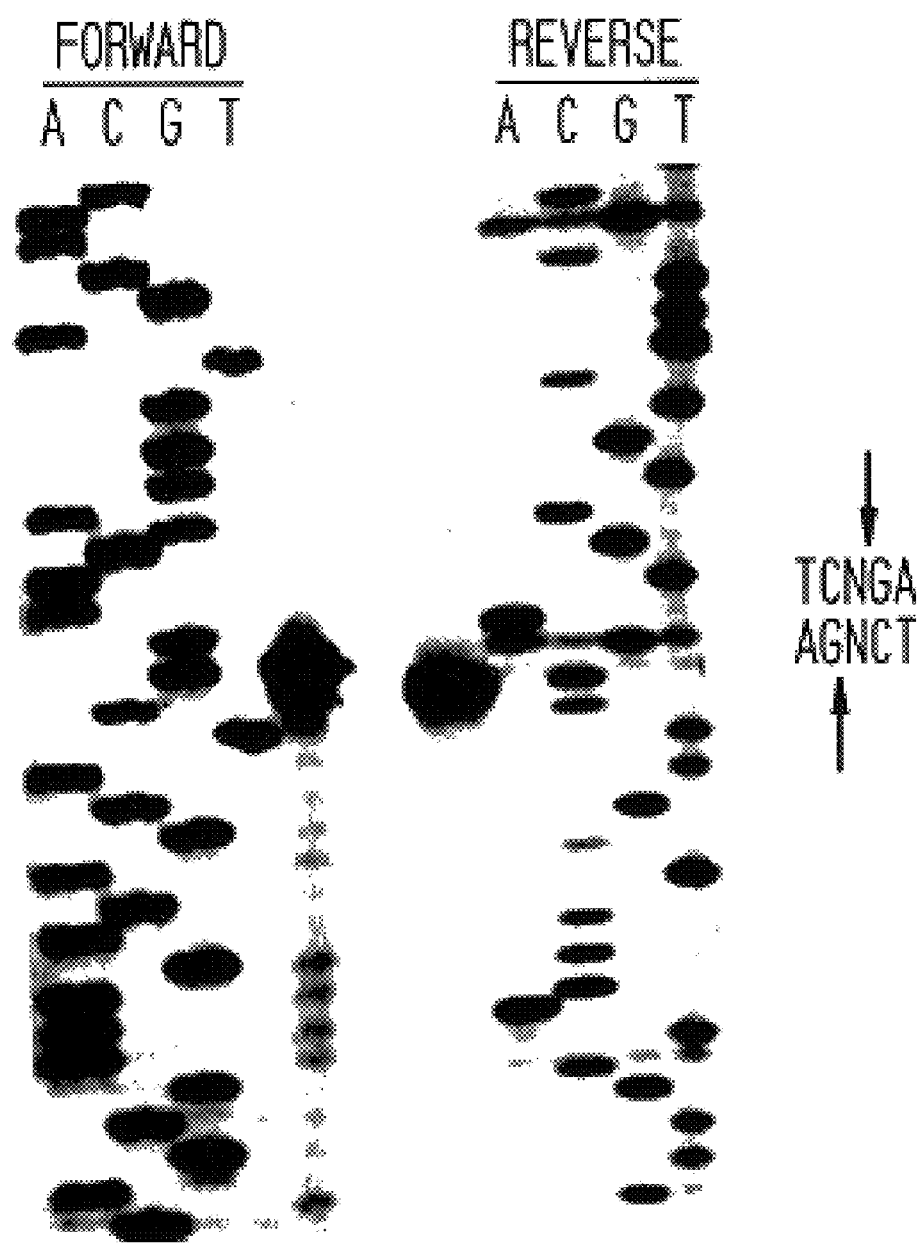
FIG. 2—Determination of the Hpy188I cleavage site.
Figure 3A:
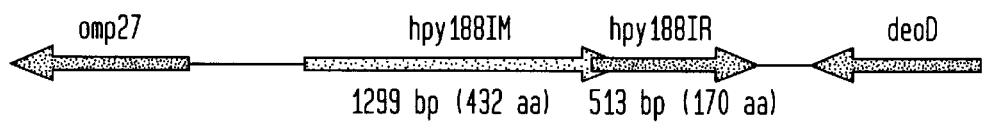
FIG. 3—Map and DNA sequence of the Hpy188I gene locus (SEQ ID NO:1, SEQ ID NO:2, SEQ ID NO:3, and SEQ ID NO:4).

Digestion of the extension reaction product from primer M13 Q1-Q2 with Hpy188I endonuclease produced a band which co-migrated with the unspecified nucleotide of the Hpy188I recognition sequence 5'-TCNGA-3' (in this case, the N is a G), indicating cleavage between the N and the G of the recognition sequence (FIG. 2, forward panel). Digestion of the extension reaction product from primer M13 Q2-2 with Hpy188I endonuclease produced a band which also co-migrated with the unspecified nucleotide of the Hpy188I recognition sequence 5'-TCNGA-3' (in this case, the N is the C on the opposite strand of DNA from the G in the M13 Q1-Q2 reaction), indicating cleavage between the N and the G of the recognition sequence on this strand of DNA as well (FIG. 2, panel B). These results indicate Hpy188I cleaves DNA between the N and G in its recognition sequence on both DNA strands, 5'-TCN/GA-3', to produce a one base 3' extension.

EXAMPLE III

Cloning the Hpy188I Endonuclease and Methylase

1. DNA purification: To prepare the genomic DNA of *Helicobacter pylori* J188, 1 gram of cell paste was resuspended in 10 ml of 25% sucrose, 0.05 M Tris-HCl pH 8.0, to which was added 5 ml of 0.25 M EDTA, pH 8.0. Then 3 ml of lysozyme solution (10 mg/ml lysozyme in 0.25 M Tris-HCl, pH 8.0) was added and the cell suspension was incubated at 4° C. for 16 hours. 12 ml of Lytic mix (1% Triton-X100, 0.05 M Tris, 62 mM EDTA, pH 8.0) and 2.5 ml of 10% SDS was then added and the solution was incubated at 37° C. for 5 minutes. The solution was extracted with one volume of equilibrated phenol:chloroform:isoamyl alcohol (50:48:2, v/v/v) and the aqueous phase was recovered and extracted with one volume of chloroform:isoamyl alcohol (24:1, v/v) two times. The aqueous solution was then dialysed against four changes of 2 L of 10 mM Tris, 1 mM EDTA, pH 8.0. The dialysed DNA solution was digested with RNase (100 µg/ml) at 37° C. for 1 hour. The DNA was precipitated by the addition of ¹⁄₁₀th volume 5 M NaCl and 0.55 volumes of 2-propanol and spooled on a glass rod. The DNA was briefly rinsed in 70% ethanol, air dried and dissolved in 3 ml TE (10 mM Tris, 1 mM EDTA, pH 8.0) to a concentration of approximately 300 mg/ml and stored at 4° C.

2. Contruction of libraries of genomic *Helicobacter pylori* J188 DNA in a selectable vector:

*Helicobacter pylori* J188 genomic DNA was partially digested with either of two frequent cutting enzymes, Sau3AI or AciI. The partial digestion was carried out by serial dilution of the Sau3AI or the AciI restriction endonuclease from 0.5 units/ag DNA to 0.016 units/µg in the manufacturer's reaction buffer and digesting at 37° C. for 1 hour. The reactions were subsequently terminated by phenol:chloroform extraction. Reactions which produced an average size range of fragments from 2 to 6 kb were used for library construction. 3 µg of this partially digested Hpy188I genomic DNA was ligated to 1 µg of the vector pUC19 (previously cleaved by BamHI (Sau3AI) or AccI (AciI) and dephosphorylated with calf intestinal alkaline phosphatase) in a final volume of 50 µl in 1×NEB ligase buffer with 1000 units (NEB) of T4 DNA ligase. The ligation reactions were incubated at 16° C. for 16 hours. 10 ul of each ligation reaction mixture was then transformed by electroporation into *E. coli* ER2683 cells and grown out in 10 ml L-Broth for 1 hour. 10 µl was then plated onto L-Broth agar plates supplemented with 100 µg/ml ampicillin to count the number transformants and the plates were incubated at 37° C. overnight. The remaining outgrowth was grown overnight in 250 ml L-Broth supplemented with 100 µg/ml ampicillin with shaking at 37° C. A total of 1×10⁶ individual transformants were obtained for the Sau3Ai library, and 6×10⁵ transformants for the AciI library. The cells of the 250 ml liquid culture were harvested by centrifugation at 5 K rpm for 5 minutes. The plasmids from these cells were purified by a standard alkaline lysis procedure, followed by four rounds of desalting in an Amicon Centricon-50 microconcentration device, washing with TE buffer each round, and then the plasmids were precipitated by PEG precipitation (combined 672 µl centricon purified plasmid, 128 µl 5 M NaCl and 800 µl 13% PEG-8000, incubated at 4° C. for 30 min, microfuged at 4° C. at maximum speed for 10 minutes, washed 2× with 70% cold ethanol) and resuspended in TE buffer at a concentration of 250 µg/ml.

3. Hpy188I methylase selection: 1 µg of the plasmid library was digested for 4 hours at 37° C. in 100 µl 1× NEB#4 buffer with 24, 12, 6 and 3 units of the Hpy188I prepared as above from *H.pylori* J188 cells. 10 µl of the Hpy188I digestion reaction was then transformed into 100 µl *E. coli* ER2688 competent cells and plated on L-broth plates containing 100 ug/ml ampicillin and the plates incubated at 37° C. overnight. A total of 24 transformants were obtained from the AciI library digested with 24 units from Hpy188I and more than 60 from the Sau3AI library. 60 of the Sau3AI library clones and 10 of the AciI library clones were analyzed as follows: Plasmid from each colony was isolated by miniprep procedures and digested with Hpy188I endonuclease.

Analysis of plasmid clones: Individual transformants were inoculated into 10 ml cultures of L-broth containing 100 μg/ml ampicillin and the plasmids that they carried were prepared by Qiagen QIAprep® Spin Miniprep columns according to the manufacturers instructions. Plasmids were assayed for the presence of the Hpy188I methylase by digestion with Hpy188I endonuclease.

3 of 60 clones analyzed from the Sau3AI library were found to be fully protected from Hpy188I digestion. Further restriction analysis showed these clones contained common Sau3AI and HindIII restriction fragments. All three clones were tested for and found to express Hpy188I restriction activity when grown in L-Broth containing 100 μg/ml ampicillin. 2 of 10 clones analyzed from the AciI library were found to be fully protected from Hpy188I digestion. Both clones were tested for and found to express Hpy188I restriction activity when grown in L-Broth containing 100 μg/ml ampicillin. One such clone was designated pHpy188IA1 (strain NEB#1175) and may be used to produce Hpy188I endonuclease by propagation to mid-log phase in a fermenter containing L-broth medium with ampicillin (100 μg/ml). The cells are harvested by centrifugation and may be stored at −20° C. or used immediately.

4. Purification of the Hpy188I restriction endonuclease from NEB #1175 can be accomplished by a combination of standard protein purification techniques, such as affinity-chromatography or ion-exchange chromatography, as outlined above. The Hpy188I restriction endonuclease obtained from this purification is substantially pure and free of non-specific endonuclease and exonuclease contamination.

EXAMPLE IV

Sequencing the Hpy188I Endonuclease and Methylase

1. DNA Sequencing: DNA sequencing, performed on double-stranded templates on an ABI automated sequencer, was based on reading of both strands and compiled with the Staden alignment programs (Staden, R. *Nuclei Acids Res.* 10:4731–4751 (1982).). Computer analyses of DNA and protein sequences were performed with the Genetics Computer Group programs (Deverenx, et al., *Nucleic Acids Res.* 12:387–395 (1984)) and database similarity searches were performed via electronic mail to the National Center for Biotechnology Information using the BLASTX algorithm (Altschul, et al., *J. Mol. Biol* 215:403–410 (1990) and Gish, et al., *Nature Genet.* 3:266 (1993)). An open reading frame (ORF) of 1299 bp which contained motifs characteristic of DNA methyl-transferases was identified and designated Hpy188IM, the Hpy188I methyl-transferase.

2. Amino terminal Hpy188I protein sequence: The approximately 19 kD protein band obtained in Example I above was subjected to amino terminal protein sequencing on an Applied BioSystems Division, Perkin-Elmer Corporation (Foster City, Calif.) Model 407A gas phase protein sequencer (Brooks, et al., *Nucleic Acids Research*, 17:979–997 (1989)). The sequence of the first 28 residues obtained was the following: (M)XKRKXDIILKSVDDLKDXIDXKDFXYK (SEQ ID NO:6). This amino acid sequence data from the amino terminus of the Hpy188I endonuclease protein matched the deduced amino acid sequence of the 513bp ORF identified in the DNA sequence of clone Hpy188IA1, which ORF is thus designated Hpy188IR, the Hpy188I endonuclease gene.

A sample of an *E. coli* containing pHpy188IA1 (NEB#1175) has been deposited under the terms and conditions of the Budapest Treaty with the American Type Culture Collection on , Sep. 9, 1999, and received ATCC Pat. Accession No. PTA-631.

---

What is claimed is:

1. Isolated DNA coding for the Hpy188I restriction endonuclease, wherein the isolated DNA is obtainable from *Helicobacter pylori* J188.

2. A recombinant DNA vector comprising a vector into which a DNA segment coding for the Hpy188I restriction endonuclease has been inserted.

3. Isolated DNA coding for the Hpy188I restriction endonuclease and methylase, wherein the isolated DNA is obtainable from ATCC No. PTA-631.

4. A cloning vector which comprises the isolated DNA of claim 3.

5. A host cell transformed by the vector of claim 2 or 4.

6. A method of producing an Hpy188I restriction endonuclease comprising culturing a host cell transformed with the vector of claim 2 or 4 under conditions suitable for expression of said endonuclease.

7. A substantially pure Type II restriction endonuclease obtainable from *Helicobacter pylori* J188 recognizing the following base sequence in double-stranded deoxyribonucleic acid molecules:

5'-TCN↓GA-3'

3'-AG↑NCT-5' and having a cleavage position defined by the arrows.

8. A method for obtaining the Type II restriction endonuclease of claim 7, comprising cultivating a sample of *Helicobacter pylori* under conditions favoring the production of said endonuclease and separating said endonuclease therefrom.

9. The Type II restriction endonuclease of claim 7, wherein the restriction endonuclease is purified from ATCC No. PTA-2878.

10. A Type II restriction endonuclease with 90% or greater amino acid sequence identity to the Type II restriction endonuclease of claim 7, obtainable from Helicobacter species.

* * * * *

UNITED STATES PATENT AND TRADEMARK OFFICE
CERTIFICATE OF CORRECTION

PATENT NO. : 6,258,583 B1
DATED : July 10, 2001
INVENTOR(S) : Richard D. Morgan and Qing Xu It is certified that error appears in the above-identified patent and that said Letters Patent is hereby corrected as shown below:

Column 1,
Line 1, insert -- A NOVEL -- before "TYPE"
Line 43, replace "assymmetric" with -- asymmetric --
Line 51, after "example" insert -- , --
Line 64, replace "ecule" with -- ecules --

Column 3,
Line 56, replace "is" with -- it --
Line 65, replace "Obtimal" with -- optimal --

Column 4,
Line 30, replace "form" with -- from --

Column 6,
Line 64, replace "dH2O" with -- $dH_2O$ --
Line 65, replace "MgC12" with -- $MgCl_2$ --

Column 7,
Line 2, replace "dH2O" with -- $dH_2O$ --
Line 4, replace "MgC12" with -- $MgCl_2$ --
Line 18, delete "to" second occurrence
Line 34, replace "an" with -- a --

UNITED STATES PATENT AND TRADEMARK OFFICE
CERTIFICATE OF CORRECTION

PATENT NO. : 6,258,583 B1
DATED : July 10, 2001
INVENTOR(S) : Richard D. Morgan and Qing Xu It is certified that error appears in the above-identified patent and that said Letters Patent is hereby corrected as shown below:

<u>Column 10,</u>
Line 2, replace "*Nuclei*" with -- *Nucl.* --
Line 9, replace "(1990)" with -- (1990)) --
Line 36, replace "on, Sep." with -- on Sep. --

Signed and Sealed this

Fifteenth Day of January, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,258,583 B1 Page 1 of 1
DATED : July 10, 2001
INVENTOR(S) : Morgan et al.

It is certified that error appears in the above-identified patent and that said Letters Patent is hereby corrected as shown below:

Column 1,
Line 6, insert -- This invention was made with Government support under contract number DK53707 awarded by the National Institutes of Health. The Government has certain rights in the invention. --

Signed and Sealed this

Twenty-eighth Day of January, 2003

JAMES E. ROGAN
*Director of the United States Patent and Trademark Office*

SEQUENCE LISTING

<160> NUMBER OF SEQ ID NOS: 7

<210> SEQ ID NO 1
<211> LENGTH: 1822
<212> TYPE: DNA
<213> ORGANISM: Helicobacter pylori
<220> FEATURE:
<221> NAME/KEY: CDS
<222> LOCATION: (52)..(1350)

<400> SEQUENCE: 1

```
tgatataatg gatttaggaa acgccaataa aattaaaaag gttcaaaaat a gtg tta      57
                                                         Val Leu
                                                           1 tct ctc cct ttg ata gaa aaa cgc cct ttt tta aat cac gaa cgc atc     105
Ser Leu Pro Leu Ile Glu Lys Arg Pro Phe Leu Asn His Glu Arg Ile
        5                  10                  15 aaa tta cat agt ttt tcg caa gtt aaa gcg tat ttt gac aca ctc aat    153
Lys Leu His Ser Phe Ser Gln Val Lys Ala Tyr Phe Asp Thr Leu Asn
     20                  25                  30 ttt gac aca agt cat ttt gtt aat tct aat gat att tgc acc cca tta   201
Phe Asp Thr Ser His Phe Val Asn Ser Asn Asp Ile Cys Thr Pro Leu
 35                  40                  45                  50
```

```
gat tgt gtg aaa gaa atg ata gac act atc cca agc gat ttt ttt aaa       249
Asp Cys Val Lys Glu Met Ile Asp Thr Ile Pro Ser Asp Phe Phe Lys
            55                  60                  65 caa gaa cat tta aaa att tta gat tgt tgt tgt ggg aat ggg aat ttt       297
Gln Glu His Leu Lys Ile Leu Asp Cys Cys Cys Gly Asn Gly Asn Phe
            70                  75                  80 ttt gct tat tta gag act aag act tct cta aac aat ctg tat ttt aat       345
Phe Ala Tyr Leu Glu Thr Lys Thr Ser Leu Asn Asn Leu Tyr Phe Asn
            85                  90                  95 gag att aac cct aaa cgc att gag cat gtt aaa aaa tat ttt ggg agc       393
Glu Ile Asn Pro Lys Arg Ile Glu His Val Lys Lys Tyr Phe Gly Ser
100                 105                 110 aat atc cat tta agc tgt aag gat ttt tta aaa ttt gat agg gct acg       441
Asn Ile His Leu Ser Cys Lys Asp Phe Leu Lys Phe Asp Arg Ala Thr
115                 120                 125                 130 ctt tat gac tta atc gtg gct aac cca cct ttt gct aaa ttt aat gcg       489
Leu Tyr Asp Leu Ile Val Ala Asn Pro Pro Phe Ala Lys Phe Asn Ala
                135                 140                 145 cta ggt cgc act tct aaa aat cat aat ctg gca aga gac ttt att aaa       537
Leu Gly Arg Thr Ser Lys Asn His Asn Leu Ala Arg Asp Phe Ile Lys
                150                 155                 160 aaa gcc tta gag ctt aca aaa aat ggg ggt tat att cta ttc att gtg       585
Lys Ala Leu Glu Leu Thr Lys Asn Gly Gly Tyr Ile Leu Phe Ile Val
            165                 170                 175 cct aat cat tgg atg agt ttt tca gat agg aat gtt tta ccc aac tta       633
Pro Asn His Trp Met Ser Phe Ser Asp Arg Asn Val Leu Pro Asn Leu
180                 185                 190 ctc tca caa tat caa ttt atc cat ctt aat att ggc gga gct aaa aaa       681
Leu Ser Gln Tyr Gln Phe Ile His Leu Asn Ile Gly Gly Ala Lys Lys
195                 200                 205                 210 tac ttt aaa aaa gtt ggc tca tct ttc act tgg ttt tta ttg caa aaa       729
Tyr Phe Lys Lys Val Gly Ser Ser Phe Thr Trp Phe Leu Leu Gln Lys
                215                 220                 225 gtc cct aat caa aaa agt ttt agc gta gaa aat cat tat gtt tta aaa       777
Val Pro Asn Gln Lys Ser Phe Ser Val Glu Asn His Tyr Val Leu Lys
                230                 235                 240 gac aga caa aga gtt tcg ctt aga act cat tta aat ttc att ccc ttg       825
Asp Arg Gln Arg Val Ser Leu Arg Thr His Leu Asn Phe Ile Pro Leu
            245                 250                 255 tat tta aac gaa ttg gtt tgt agc att tta gat aaa acg atc aat aat       873
Tyr Leu Asn Glu Leu Val Cys Ser Ile Leu Asp Lys Thr Ile Asn Asn
260                 265                 270 act cat tta cct acc tat aaa ata gaa acg aca agc ttt cta cac agg       921
Thr His Leu Pro Thr Tyr Lys Ile Glu Thr Thr Ser Phe Leu His Arg
275                 280                 285                 290 aca acc aag aaa gaa ttt tta tcg ccc att caa aat aag gac tac cct       969
Thr Thr Lys Lys Glu Phe Leu Ser Pro Ile Gln Asn Lys Asp Tyr Pro
                295                 300                 305 tat aag att atc cat acc cct agt caa gtc gta tat agt aaa atc ccc      1017
Tyr Lys Ile Ile His Thr Pro Ser Gln Val Val Tyr Ser Lys Ile Pro
                310                 315                 320 cac aaa tac caa gaa ggc tat aaa gtc ttt tta tct ttg act aat caa      1065
His Lys Tyr Gln Glu Gly Tyr Lys Val Phe Leu Ser Leu Thr Asn Gln
            325                 330                 335 tac agc aca ttt att gat aat tgc ggc atg aca caa agc att gcg ttt      1113
Tyr Ser Thr Phe Ile Asp Asn Cys Gly Met Thr Gln Ser Ile Ala Phe
            340                 345                 350 gtg cgt tgc aaa aac tac gaa gag gcc tta aaa att aaa acc gaa tta      1161
Val Arg Cys Lys Asn Tyr Glu Glu Ala Leu Lys Ile Lys Thr Glu Leu
355                 360                 365                 370
```

```
gat aat gag att tat tta ttt ctt aat aat ctc act cgt tat gga aat    1209
Asp Asn Glu Ile Tyr Leu Phe Leu Asn Asn Leu Thr Arg Tyr Gly Asn
            375                 380                 385 ttt aat aac att aga gtg tta cag cat tta cct tta tta gaa agt att    1257
Phe Asn Asn Ile Arg Val Leu Gln His Leu Pro Leu Leu Glu Ser Ile
            390                 395                 400 gtt cta aac aag caa gaa tta gaa ttt atc caa aaa ttt aat gag gcg    1305
Val Leu Asn Lys Gln Glu Leu Glu Phe Ile Gln Lys Phe Asn Glu Ala
            405                 410                 415 tat tat ggc aaa aag aaa gag cga tat aat ttt aaa gag tgt tga        1350
Tyr Tyr Gly Lys Lys Lys Glu Arg Tyr Asn Phe Lys Glu Cys
        420                 425                 430 tgatttaaaa gatgaaattg attacaagga ctttgaatac aaagagtatt ttaatttatt   1410
atgcgaatta gtccctaata atagtttgga aaaattagaa atcaacgcca ttgatgaaaa   1470
gaatatgaaa aacgaaggac ttgtatatgt gtttgttatt caaggtaaaa ttttaaaat    1530 cggtcatagt attacgccca tcacaaagcg agtgcaatct tataattgcg gcaaagtaga   1590
atatcgtaaa aatggcactt gctccacaac aaattatttt gtattgcaat cgctcttaaa   1650
gattaataaa atcgtacaag tgtatgcatt ttttccagaa caacctacct ataccctatt   1710
tggtaaaact taccaagata gtttttcaac ttctaaaagg gctgagaatg tgattttaga   1770
aaattttatt aaaaatcata ataaaaaacc tatcggatgc acacagactt aa           1822

<210> SEQ ID NO 2
<211> LENGTH: 432
<212> TYPE: PRT
<213> ORGANISM: Helicobacter pylori

<400> SEQUENCE: 2

Val Leu Ser Leu Pro Leu Ile Glu Lys Arg Pro Phe Leu Asn His Glu
  1               5                  10                  15

Arg Ile Lys Leu His Ser Phe Ser Gln Val Lys Ala Tyr Phe Asp Thr
             20                  25                  30

Leu Asn Phe Asp Thr Ser His Phe Val Asn Ser Asn Asp Ile Cys Thr
         35                  40                  45

Pro Leu Asp Cys Val Lys Glu Met Ile Asp Thr Ile Pro Ser Asp Phe
     50                  55                  60

Phe Lys Gln Glu His Leu Lys Ile Leu Asp Cys Cys Cys Gly Asn Gly
 65                  70                  75                  80

Asn Phe Phe Ala Tyr Leu Glu Thr Lys Thr Ser Leu Asn Asn Leu Tyr
                 85                  90                  95

Phe Asn Glu Ile Asn Pro Lys Arg Ile Glu His Val Lys Lys Tyr Phe
            100                 105                 110

Gly Ser Asn Ile His Leu Ser Cys Lys Asp Phe Leu Lys Phe Asp Arg
        115                 120                 125

Ala Thr Leu Tyr Asp Leu Ile Val Ala Asn Pro Pro Phe Ala Lys Phe
    130                 135                 140

Asn Ala Leu Gly Arg Thr Ser Lys Asn His Asn Leu Ala Arg Asp Phe
145                 150                 155                 160

Ile Lys Lys Ala Leu Glu Leu Thr Lys Asn Gly Gly Tyr Ile Leu Phe
                165                 170                 175

Ile Val Pro Asn His Trp Met Ser Phe Ser Asp Arg Asn Val Leu Pro
            180                 185                 190

Asn Leu Leu Ser Gln Tyr Gln Phe Ile His Leu Asn Ile Gly Gly Ala
        195                 200                 205
```

-continued

```
Lys Lys Tyr Phe Lys Lys Val Gly Ser Ser Phe Thr Trp Phe Leu Leu
    210                 215                 220
Gln Lys Val Pro Asn Gln Lys Ser Phe Ser Val Glu Asn His Tyr Val
225                 230                 235                 240
Leu Lys Asp Arg Gln Arg Val Ser Leu Arg Thr His Leu Asn Phe Ile
                245                 250                 255
Pro Leu Tyr Leu Asn Glu Leu Val Cys Ser Ile Leu Asp Lys Thr Ile
            260                 265                 270
Asn Asn Thr His Leu Pro Thr Tyr Lys Ile Glu Thr Thr Ser Phe Leu
        275                 280                 285
His Arg Thr Thr Lys Lys Glu Phe Leu Ser Pro Ile Gln Asn Lys Asp
290                 295                 300
Tyr Pro Tyr Lys Ile Ile His Thr Pro Ser Gln Val Val Tyr Ser Lys
305                 310                 315                 320
Ile Pro His Lys Tyr Gln Glu Gly Tyr Lys Val Phe Leu Ser Leu Thr
                325                 330                 335
Asn Gln Tyr Ser Thr Phe Ile Asp Asn Cys Gly Met Thr Gln Ser Ile
            340                 345                 350
Ala Phe Val Arg Cys Lys Asn Tyr Glu Glu Ala Leu Lys Ile Lys Thr
        355                 360                 365
Glu Leu Asp Asn Glu Ile Tyr Leu Phe Leu Asn Asn Leu Thr Arg Tyr
370                 375                 380
Gly Asn Phe Asn Asn Ile Arg Val Leu Gln His Leu Pro Leu Leu Glu
385                 390                 395                 400
Ser Ile Val Leu Asn Lys Gln Glu Leu Glu Phe Ile Gln Lys Phe Asn
                405                 410                 415
Glu Ala Tyr Tyr Gly Lys Lys Lys Glu Arg Tyr Asn Phe Lys Glu Cys
            420                 425                 430

<210> SEQ ID NO 3
<211> LENGTH: 1822
<212> TYPE: DNA
<213> ORGANISM: Helicobacter pylori
<220> FEATURE:
<221> NAME/KEY: CDS
<222> LOCATION: (1310)..(1819)

<400> SEQUENCE: 3
tgatataatg gatttaggaa acgccaataa aattaaaaag gttcaaaaat agtgttatct      60
ctccctttga tagaaaaacg cccttttttta aatcacgaac gcatcaaatt acatagtttt    120
tcgcaagtta aagcgtattt tgacacactc aattttgaca caagtcattt tgttaattct    180
aatgatattt gcaccccatt agattgtgtg aaagaaatga tagacactat cccaagcgat    240
ttttttaaac aagaacattt aaaaatttta gattgttgtt gtgggaatgg gaattttttt    300
gcttatttag agactaagac ttctctaaac aatctgtatt ttaatgagat taaccctaaa    360
cgcattgagc atgttaaaaa atattttggg agcaatatcc atttaagctg taaggatttt    420
ttaaaatttg atagggctac gctttatgac ttaatcgtgg ctaacccacc ttttgctaaa    480
tttaatgcgc taggtcgcac ttctaaaaat cataatctgg caagagactt tattaaaaaa    540
gccttagagc ttacaaaaaa tgggggttat attctattca ttgtgcctaa tcattggatg    600 agttttcag ataggaatgt tttacccaac ttactctcac aatatcaatt tatccatctt    660
aatattggcg gagctaaaaa atactttaaa aaagttggct catctttcac ttggtttta    720 ttgcaaaaag tccctaatca aaaagttttt agcgtagaaa atcattatgt tttaaaagac    780
```

```
agacaaagag tttcgcttag aactcattta aatttcattc ccttgtattt aaacgaattg    840
gtttgtagca ttttagataa aacgatcaat aatactcatt tacctaccta taaaatagaa    900
acgacaagct ttctacacag gacaaccaag aaagaatttt tatcgcccat tcaaaataag    960 gactacccctt ataagattat ccatacccct agtcaagtcg tatatagtaa aatcccccac   1020
aaataccaag aaggctataa agtcttttta tctttgacta atcaatacag cacatttatt   1080
gataattgcg gcatgacaca aagcattgcg tttgtgcgtt gcaaaaacta cgaagaggcc   1140
ttaaaaatta aaaccgaatt agataatgag atttatttat ttcttaataa tctcactcgt   1200
tatggaaatt ttaataacat tagagtgtta cagcatttac ctttattaga aagtattgtt   1260
ctaaacaagc aagaattaga atttatccaa aaatttaatg aggcgtatt atg gca aaa   1318
                                                        Met Ala Lys
                                                          1
```

```
aga aag agc gat ata att tta aag agt gtt gat gat tta aaa gat gaa    1366
Arg Lys Ser Asp Ile Ile Leu Lys Ser Val Asp Asp Leu Lys Asp Glu
  5                  10                  15 att gat tac aag gac ttt gaa tac aaa gag tat ttt aat tta tta tgc    1414
Ile Asp Tyr Lys Asp Phe Glu Tyr Lys Glu Tyr Phe Asn Leu Leu Cys
 20                  25                  30                  35 gaa tta gtc cct aat aat agt ttg gaa aaa tta gaa atc aac gcc att    1462
Glu Leu Val Pro Asn Asn Ser Leu Glu Lys Leu Glu Ile Asn Ala Ile
                 40                  45                  50 gat gaa aag aat atg aaa aac gaa gga ctt gta tat gtg ttt gtt att    1510
Asp Glu Lys Asn Met Lys Asn Glu Gly Leu Val Tyr Val Phe Val Ile
             55                  60                  65 caa ggt aaa att ttt aaa atc ggt cat agt att acg ccc atc aca aag    1558
Gln Gly Lys Ile Phe Lys Ile Gly His Ser Ile Thr Pro Ile Thr Lys
         70                  75                  80 cga gtg caa tct tat aat tgc ggc aaa gta gaa tat cgt aaa aat ggc    1606
Arg Val Gln Ser Tyr Asn Cys Gly Lys Val Glu Tyr Arg Lys Asn Gly
     85                  90                  95 act tgc tcc aca aca aat tat ttt gta ttg caa tcg ctc tta aag att    1654
Thr Cys Ser Thr Thr Asn Tyr Phe Val Leu Gln Ser Leu Leu Lys Ile
100                 105                 110                 115 aat aaa atc gta caa gtg tat gca ttt ttt cca gaa caa cct acc tat    1702
Asn Lys Ile Val Gln Val Tyr Ala Phe Phe Pro Glu Gln Pro Thr Tyr
                120                 125                 130 acc cta ttt ggt aaa act tac caa gat agt ttt tca act tct aaa agg    1750
Thr Leu Phe Gly Lys Thr Tyr Gln Asp Ser Phe Ser Thr Ser Lys Arg
            135                 140                 145 gct gag aat gtg att tta gaa aat ttt att aaa aat cat aat aaa aaa    1798
Ala Glu Asn Val Ile Leu Glu Asn Phe Ile Lys Asn His Asn Lys Lys
        150                 155                 160 cct atc gga tgc aca cag act taa                                    1822
Pro Ile Gly Cys Thr Gln Thr
    165                 170
```

<210> SEQ ID NO 4
<211> LENGTH: 170
<212> TYPE: PRT
<213> ORGANISM: Helicobacter pylori

<400> SEQUENCE: 4

Met Ala Lys Arg Lys Ser Asp Ile Ile Leu Lys Ser Val Asp Asp Leu
  1               5                  10                  15

Lys Asp Glu Ile Asp Tyr Lys Asp Phe Glu Tyr Lys Glu Tyr Phe Asn
             20                  25                  30

```
Leu Leu Cys Glu Leu Val Pro Asn Asn Ser Leu Glu Lys Leu Glu Ile
        35                  40                  45

Asn Ala Ile Asp Glu Lys Asn Met Lys Asn Glu Gly Leu Val Tyr Val
        50                  55                  60

Phe Val Ile Gln Gly Lys Ile Phe Lys Ile Gly His Ser Ile Thr Pro
 65                  70                  75                  80

Ile Thr Lys Arg Val Gln Ser Tyr Asn Cys Gly Lys Val Glu Tyr Arg
                 85                  90                  95

Lys Asn Gly Thr Cys Ser Thr Thr Asn Tyr Phe Val Leu Gln Ser Leu
                100                 105                 110

Leu Lys Ile Asn Lys Ile Val Gln Val Tyr Ala Phe Phe Pro Glu Gln
        115                 120                 125

Pro Thr Tyr Thr Leu Phe Gly Lys Thr Tyr Gln Asp Ser Phe Ser Thr
130                 135                 140

Ser Lys Arg Ala Glu Asn Val Ile Leu Glu Asn Phe Ile Lys Asn His
145                 150                 155                 160

Asn Lys Lys Pro Ile Gly Cys Thr Gln Thr
                165                 170

<210> SEQ ID NO 5
<211> LENGTH: 20
<212> TYPE: DNA
<213> ORGANISM: Helicobacter pylori

<400> SEQUENCE: 5
ggtcgctgag gcttgcaggg                                                20

<210> SEQ ID NO 6
<211> LENGTH: 28
<212> TYPE: PRT
<213> ORGANISM: Helicobacter pylori
<220> FEATURE:
<223> OTHER INFORMATION: At positions 2, 6, 19, 22 and 26 "Xaa" =
      any amino acid

<400> SEQUENCE: 6

Met Xaa Lys Arg Lys Xaa Asp Ile Ile Leu Lys Ser Val Asp Asp Leu
 1               5                  10                  15

Lys Asp Xaa Ile Asp Xaa Lys Asp Phe Xaa Tyr Lys
             20                  25

<210> SEQ ID NO 7
<211> LENGTH: 20
<212> TYPE: DNA
<213> ORGANISM: Helicobacter pylori

<400> SEQUENCE: 7
cgtttaatgg aaacttcctc                                                20
```